United States Patent
Collins (10) Patent No.: US 7,262,703 B2
(45) Date of Patent: Aug. 28, 2007

(54) SYSTEM FOR GENERATING A SIGNAL INDICATIVE OF A STATE OF A USER'S BODY

(76) Inventor: John Collins, 300 Elfwood Dr., Monrovia, CA (US) 91016

( * ) Notice: Subject to any disclaimer, the term of this patent is extended or adjusted under 35 U.S.C. 154(b) by 189 days.

(21) Appl. No.: 10/911,292

(22) Filed: Aug. 4, 2004

(65) Prior Publication Data

US 2006/0033626 A1     Feb. 16, 2006

(51) Int. Cl.
*G08B 23/00* (2006.01)

(52) U.S. Cl. .............................. 340/573.1; 340/539.12; 600/372; 600/393

(58) Field of Classification Search .............. 340/573.1
See application file for complete search history.

(56) References Cited

U.S. PATENT DOCUMENTS

| | | | | |
|---|---|---|---|---|
| 5,579,782 | A * | 12/1996 | Masuo ........................ | 600/547 |
| 5,817,031 | A * | 10/1998 | Masuo et al. ................ | 600/547 |
| 6,243,651 | B1 * | 6/2001 | Masuo ......................... | 702/19 |
| 6,353,755 | B1 * | 3/2002 | Oguma ........................ | 600/547 |
| 6,400,983 | B1 * | 6/2002 | Cha ............................. | 600/547 |
| 6,459,930 | B1 * | 10/2002 | Takehara et al. ............ | 600/547 |
| 6,643,543 | B2 * | 11/2003 | Takehara et al. ............ | 600/547 |
| 6,690,181 | B1 * | 2/2004 | Dowdeswell et al. ........ | 324/691 |
| 6,725,089 | B2 * | 4/2004 | Komatsu et al. ............. | 600/547 |
| 6,748,264 | B2 * | 6/2004 | Chai ............................ | 600/546 |
| 6,850,797 | B2 * | 2/2005 | Kawanishi et al. .......... | 600/547 |
| 6,920,352 | B2 * | 7/2005 | Shimomura et al. ......... | 600/547 |
| 6,963,035 | B2 * | 11/2005 | Honda et al. ............. | 177/25.19 |
| 2004/0077969 | A1 * | 4/2004 | Onda et al. .................. | 600/547 |

\* cited by examiner

*Primary Examiner*—Benjamin C. Lee
*Assistant Examiner*—Eric M. Blount
(74) *Attorney, Agent, or Firm*—Wood, Phillips, Katz, Clark & Mortimer (57) ABSTRACT

A system for generating a signal indicative of a state of a user's body. The system has a housing assembly and first and second spaced electrodes on the housing situated so that an electrical impulse can be generated a) through the first electrode to a first user appendage in operative contact with the first electrode and b) from a second user appendage in operative contact with the second electrode to the second electrode, to thereby allow generation of a user impedance signal. The user impedance signal is useable to identify a state of a user's body. The housing has an electrically insulating barrier assembly defined between first and second discrete contours at or adjacent to which the first and second electrodes are respectively located. The insulating barrier assembly resides between first and second user appendages in operative contact with the first and second electrodes so as to block direct contact between the first and second user appendages.

39 Claims, 8 Drawing Sheets

SYSTEM FOR GENERATING A SIGNAL INDICATIVE OF A STATE OF A USER'S BODY

BACKGROUND OF THE INVENTION

1. Field of the Invention

This invention relates to physiological health monitoring and, more particularly, to a system through which a state of a user's body can be ascertained.

2. Background Art

The state of the health of the overall population in the U.S. and in other countries is becoming increasingly troubling. Technology has facilitated productivity while permitting a sedentary lifestyle. Executives and employees now have the capability of performing a wide range of tasks worldwide while seated at a desk in front of a computer. Technology has afforded both young and old the opportunity to assimilate vast amounts of information through web accessible sources. Additionally, technological advances have made available a wide range of entertainment through information access, music, video games, etc. Interest in this entertainment spans all age groups.

While modern technology has made available resources for business and recreational purposes to all ages, exploitation of these resources often leads to a reduction in the amount of physical activity that persons engage in. The trend in the younger age groups has been to seek entertainment through technology rather than through physical activity. This has contributed to a rise in obesity which is now reaching epidemic proportions. Articles abound reporting trends in obesity, which have potential serious short and long term consequences.

Even in young persons, obesity may contribute to short and long term health and medically-related problems. Obesity may interfere with the physical and psychological development of young persons, often impairing their ability to interact in a positive way with others, and leading to psychological problems, including depression. In older age groups, some of these same problems arise. Additionally, for all ages productivity may be seriously impaired.

At the business level, consequences of obesity are even more severe. The ability of an organization to obtain medical benefits may be impaired by persons in a high risk medical category, such as obesity. It is no secret that the nation is approaching a crisis level in terms of making healthcare available to its work force.

The problem with obesity is further aggravated by the fact that technology, while offering opportunities for increased productivity, also increases expectations and demands on those in business, from top to bottom. These demands translate into additional working hours which represent even more physical "down time".

Extended hours reduce the amount of people's free time. This encourages the need for efficiency, which in turn leads to the frequenting of fast food establishments and the consumption of foods that are convenient, but often not healthy. This trend has contributed to obesity in all age groups.

There has of late been an increasing awareness of the impact that obesity, and other physical health-related problems, induced by poor nutrition and inactive lifestyles, is having on the population as a whole. Healthcare costs are soaring. The cost of medical insurance for individuals in business is increasing at an alarming rate to the point that profitability is being affected. Further, the ability of a business to attract quality persons is often significantly affected by whether or not that business can provide to its employees an attractive and competitive benefits package.

Aside from the direct costs associated with medical problems, there is a loss of revenue due to reduced productivity. Those with health-related problems tend to account for a high level of absenteeism. Further, physical and mental capacities may be diminished in those individuals that are suffering from a health-related problem.

The recognition of the problems associated with the progressive diminishing of the population's health level has spurred an interest in reversing the above trends. Fast food establishments have been pressured into offering foods that are "fast" but at the same time in a healthier category.

More significantly, there has been an emphasis on encouraging individual accountability for a healthier lifestyle and maintenance of good health. Ideally, individuals would be able to regularly assess their own health-level to both motivate themselves to continue progressively towards improved health and identify health-related problems.

Generally, health monitoring has been achieved through periodic physical exams conducted by a medical doctor. Typically, these "physicals" are scheduled on an annual basis or potentially even less frequently. In between visits to a doctor, individuals may have few definable goals that motivate them to engage in a change in lifestyle that will improve overall health. For a large percentage of the population, there may be a small window of motivation to improve immediately following a medical examination. This motivation tends to wane significantly thereafter and up to the following medical visit.

The assignee herein has developed an extensive program to allow individuals to assess their own health on an ongoing and regular basis. One aspect of this program is carried out interactively online, as described in U.S. patent application Ser. No. 09/518,781. Through this system, individuals are allowed to take measurements of various health-related attributes and determine progress towards better health by identifying problems or potential problems associated with their health.

One aspect of health assessment in the above program is the determination of body composition, which includes determination of percentages of lean muscle, fat, and water. Most commonly, these measurements are taken through a "dunk test" which requires body immersion. Clearly, it is not practical to conduct this test on a regular basis.

The assignee here has devised an instrument that is capable of generating these same measurements to substantially the same accuracy through a bio-impedance measurement. This instrument has been commercially sold under the trademark "BC1" and is also described in U.S. patent application Ser. No. 09/518,781.

The BC1 instrument is designed with a housing having a generally cylindrical shape. The housing has axially facing walls with each supporting a plurality of electrodes. A measurement is taken by the user by having the user place his/her hands one against the electrodes at each of the walls. The housing is made with a sufficient axial extent that the electrodes can be comfortably engaged without inadvertent contact occurring between the user's hands, as would preclude a proper impedance measurement.

The BC1 instrument, in its current configuration, has been well accepted commercially. The instrument is designed to operate either in a stand alone capacity or be web-enabled to allow body composition measurements to be taken and interactively processed and analyzed. The only limitation with respect to this instrument is that the housing size and shape make it somewhat inconvenient to store and operate on a desk, counter, or the like, where space is at a premium. Ideally, the instrument would be compact and aesthetically pleasing to be kept at a location whereat it would be regularly used, such as at an executive's or employee's desk, on a counter, adjacent to a computer terminal, etc. Thus, ideally, the instrument would be kept in an operative state to be readily accessed and operated to take body state measurements so as to encourage regular health monitoring.

SUMMARY OF THE INVENTION

In one form, the invention is directed to a system for generating a signal indicative of a state of a user's body. The system has a housing assembly and first and second spaced electrodes on the housing situated so that an electrical impulse can be generated a) through the first electrode to a first user appendage in operative contact with the first electrode and b) from a second user appendage in operative contact with the second electrode to the second electrode, to thereby allow generation of a user impedance signal. The user impedance signal is useable to identify a state of a user's body. The housing has an electrically insulating barrier assembly defined between first and second discrete contours at or adjacent to which the first and second electrodes are respectively located. The insulating barrier assembly resides between first and second user appendages in operative contact with the first and second electrodes so as to block direct contact between the first and second user appendages.

In one form, the first discrete contour has a surface around which a user's fingers on one hand can be wrapped with the user's one hand in operative contact with the first electrode.

The first discrete contour may be configured to be graspable operably between the a) fingers and b) palm and/or thumb on a hand of a user.

In one form, the housing assembly has a front and rear and the first electrode is on one of the front and rear of the housing.

In one form, there is a third electrode on the other of the front and rear of the housing and the first discrete contour is configured to be graspable operatively between the a) fingers and b) palm and/or thumb on a hand of a user.

In one form, with a user operatively grasping the first discrete contour, the first electrode is operatively contacted by at least one of a user's fingers and the third electrode is operatively contacted by a user's palm and/or thumb.

The first electrode may be located to be operatively contacted by one of a) the palm and/or thumb and b) at least one finger on a hand that is operatively grasping the first discrete contour.

In one form, the housing assembly has an upright wall and a transverse base. The first and second electrodes are on the upright wall. The transverse base defines a surface to bear on a subjacent support to maintain the housing assembly in an operative orientation.

The housing assembly has a front and rear and spaced sides. In one form, the upright wall and transverse base define one of an "L" or a "U" shape as viewed from the side of the housing assembly.

The first discrete contour may have a convexly curved surface.

The convexly curved surface may have an effective diameter of not greater than two (2) inches.

In one form the convexly curved surface extends through in excess of 180° around a center line for the curved surface.

The system may further have a generator for an electrical impulse on the housing assembly to be directed through the first electrode.

The system may further include a generator for the user impedance signal on the housing assembly.

The system may be further provided in combination with a means for converting the user impedance signal to a human readable form.

The converting means may convert the user impedance signal to a measurement that is at least one of a user's percentage of a) body water, b) body fat, and c) lean muscle mass.

The converting means may include at least one of a personal computer and a web server.

The system may be further provided in combination with an independently operable device that is mounted to the housing assembly.

The independently operable device may be a docking station for an instrument to measure a health-related attribute of a user.

Alternatively, the independently operable device may be a desk accessory.

The invention is further directed to a system for generating a signal indicative of a state of a user's body. The system has a housing assembly and first and second spaced electrodes on the housing assembly situated so that an electrical impulse can be generated a) through the first electrode to a first user appendage in operative contact with the first electrode and b) from a second user appendage in operative contact with the second electrode to the second electrode to thereby allow generation of a user impedance signal. The user impedance signal is useable to identify a state of a user's body. The housing assembly has first and second contours that can be operatively grasped, one each in the hand of a user, so as to allow each hand to operatively contact one of the electrodes while avoiding direct contact between the hands operatively grasping the first and second contours.

The first and second contours may be discrete contours.

In one form, the first contour has a surface around which a user's fingers on one hand can be wrapped with the user's one hand in operative contact with the first electrode.

The first contour may be configured to be graspable operatively between the a) fingers and b) palm and/or thumb on a hand of a user.

In one form, the housing assembly has a front and rear and the first electrode is on one of the front and rear of the housing.

In one form, there is a third electrode on the other of the front and rear of the housing and the first discrete contour is configured to be graspable operatively between the a) fingers and b) palm and/or thumb on a hand of a user.

In one form, with a user operatively grasping the first discrete contour, the first electrode is operatively contacted by at least one of a user's fingers and the third electrode is operatively contacted by a user's palm and/or thumb.

In one form, the first electrode is located to be operatively contacted by one of a) the palm and/or thumb and b) at least one finger on a hand that is operatively grasping the first contour.

In one form, the housing assembly has an upright wall and a transverse base. The first and second electrodes are on the upright wall and the transverse base defines a surface to bear on a subjacent support to maintain the housing assembly in an operative orientation.

In one form, the housing assembly has a front and rear and spaced sides and the upright wall and transverse base define one of an "L" or a "U" shape as viewed from the side of the housing assembly.

The first contour may have a convexly curved surface.

The convexly curved surface may have an effective diameter of not greater than two (2) inches.

In one form, the convexly curved surface extends through in excess of 180° around a centerline for the curved surface.

The system may further have a generator for an electrical impulse on the housing assembly to be directed through the first electrode.

The system may further include a generator for the user impedance signal on the housing assembly.

The system may be further provided in combination with a means for converting the user impedance signal to a human readable form.

The converting means may convert the user impedance signal to a measurement that is at least one of a user's percentage of a) body water, b) body fat, and c) lean muscle mass.

The converting means may include at least one of a personal computer and a web server.

The system may be further provided in combination with an independently operable device that is mounted to the housing assembly.

The independently operable device may be a docking station for an instrument to measure a health-related attribute of a user.

Alternatively, the independently operable device may be a desk accessory.

In one form, the housing assembly has an electrically insulating barrier assembly that resides between fingers on a user's hands that are operatively grasping the first and second contours.

DETAILED DESCRIPTION OF THE DRAWINGS

Figure 1:
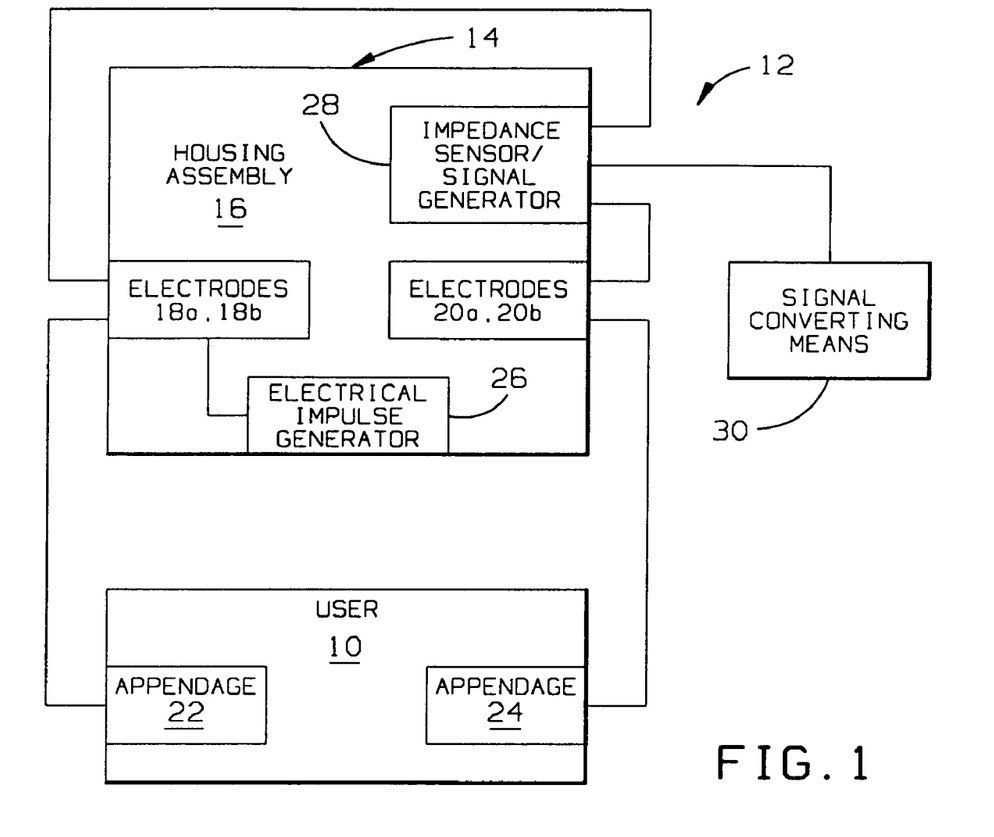
FIG. 1 is a schematic representation of one form of system for generating a signal indicative of a state of a user's body, according to the present invention.

In FIG. 1, a schematic representation of a system for generating a signal, indicative of a state of a body of a user 10, according to the present invention, is shown at 12. The system 12 consists of an instrument/subsystem 14 that is capable of generating a signal derived through measurement of physical characteristics of the user 10. This signal can be processed to identify a health-related attribute for the user 10.

In an exemplary form, the subsystem 14 consists of a housing assembly 16, upon which first and second spaced electrode pairs 18, 20 are provided. The first electrode pair 18 consists of front and rear mounted electrodes 18a, 18b, respectively. The second electrode pair 20 consists of front and rear mounted electrodes 20a, 20b, respectively. The electrodes 18a, 18b, 20a, 20b may all be made from a conductive material, such as brushed stainless steel. As explained in greater detail below, the electrode pairs 18, 20 are situated so that one, and preferably both, of the electrodes 18a 18b, can be operatively contacted by one user appendage 22, and one, and preferably both, of the electrodes 20a, 20b, can be contacted by another appendage 24 of the user. With the appendages 22, 24 in operative contact with the electrode pairs 18, 20, respectively, an electrical impulse is produced through a generator 26 to either of the electrode pairs 18, 20, in this case shown as the electrode pair 18. The electrical impulse generated to the electrode pair 18 is directed to the user's one appendage 22 in operative contact with the electrode pair 18 and through the user's body and from the user's other appendage 22 to the electrode pair 18 in which the user's other appendage 24 is in operative contact.

Through an impedance sensor/signal generator 28, processing of this electrical impulse transmission is carried out and a signal, representative of the user's bio-impedance, is generated. The precise structure of the impedance sensor/signal generator 28 is not critical to the present invention. The impedance sensor/signal generator 28 may be made up of several, separate components, or as an integrated unit. The resulting signal may be displayed in human readable form for analysis. Alternatively, the signal generated by the impedance sensor/signal generator 28 may be in non-human readable form, whereby it is required to be converted to human readable form by a means shown at 30. The signal converting means 30 may be part of a stand alone system, such as a personal computer, or may be a web server or other structure known to those skilled in the art. The entire system 12 may be "stand alone" or a system that is an on-line interactive system using a web server, as described in U.S. patent application Ser. No. 09/518,781, which is incorporated herein by reference.

Figure 2:
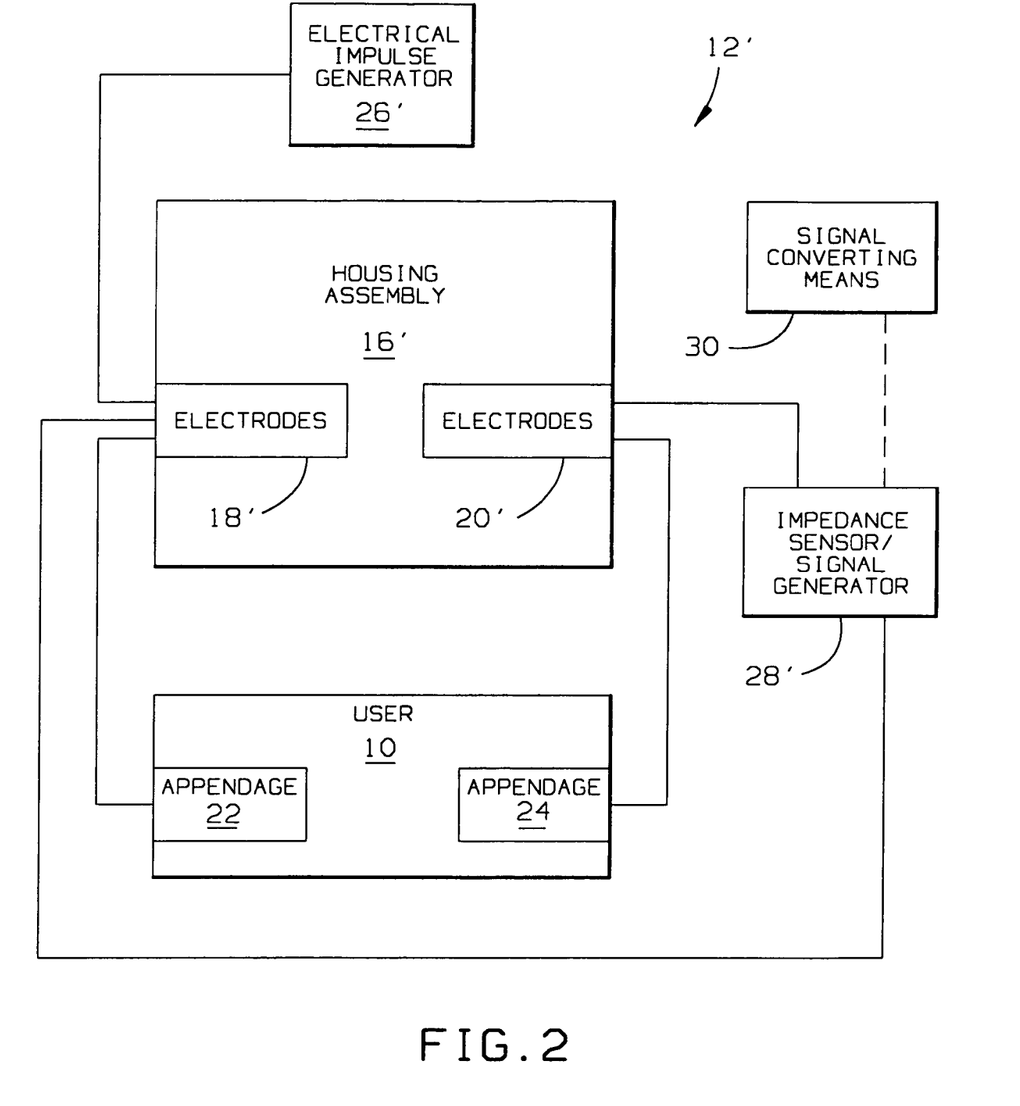
FIG. 2 is a view as in FIG. 1 of a modified form of the inventive system.

In an alternative form, shown in FIG. 2, the inventive system 12' consists of a housing assembly 16' with spaced electrode pairs 18', 20'. In this embodiment, the electrical impulse generator 26' is external to the housing assembly 16', as is the impedance signal generator 28'. From the standpoint of the user 10, the operation of the system 12' is the same as the operation of the system 12. That is, the user 10 places his/her appendages 22, 24, one each, in operative contact with one or both of the electrodes in the pairs 18', 20'. Through the electrical impulse generator 26', an impedance signal can be produced by the generator 28' that is in either human readable form or must be converted, as by the aforementioned signal converting means 30.

Details of the operation of the systems 12, 12' will be described hereinbelow. The principal focus of the present invention is on the configuration of the housing assemblies 16, 16' on which the electrode pairs 18, 18', 20, 20' are provided. The precise manner of generating the electrical impulse and impedance signal are not critical to the present invention. For purposes of simplicity, the invention will be described with respect to the representative system 12.

As seen in FIGS. 3-8, in one form, the housing assembly 16 consists of a front, upright wall 34 and a transverse base 36. As viewed from the side of the housing assembly 16, the upright wall 34 and transverse base 36 together define a generally "U" shape, with the upright wall 34 angled back, from bottom to top, so that a center plane P (FIG. 5), between the front and rear of the upright wall 34, makes an angle α with a reference plane containing a flat subjacent support surface 38 against which a downwardly facing surface 40 on the transverse base 36 facially abuts to maintain the housing assembly 16 in an operative orientation. Alternatively, as shown in dotted lines in FIG. 5, the upright wall 34a may be vertically oriented so as to define an "L" shape in conjunction with the base 36.

The housing assembly 16 has first and second discrete contours, 42, 44 which blend into a web 46 at the front wall 34. The housing assembly 16 is symmetrical about a vertical plane P1 (FIG. 6), extending in a fore-and-aft direction midway between the first and second contours 42, 44.

The exemplary contour 44 has a generally circular/elliptical shape as viewed in cross section defined by a horizontal plane. The effective diameter D (FIG. 7) of this shape is preferably less than two (2) inches, though this is not a requirement. The electrode 20a is elongate, with a length that extends in an upward direction on the second contour 44 at the front thereof, with the electrode 20b extending likewise at the rear of the second contour 44. The contour 44 has a curved peripheral surface 50 that can be comfortably operatively grasped/engaged by the user's appendage 24, shown in this case as the user's right hand.

Figure 7:
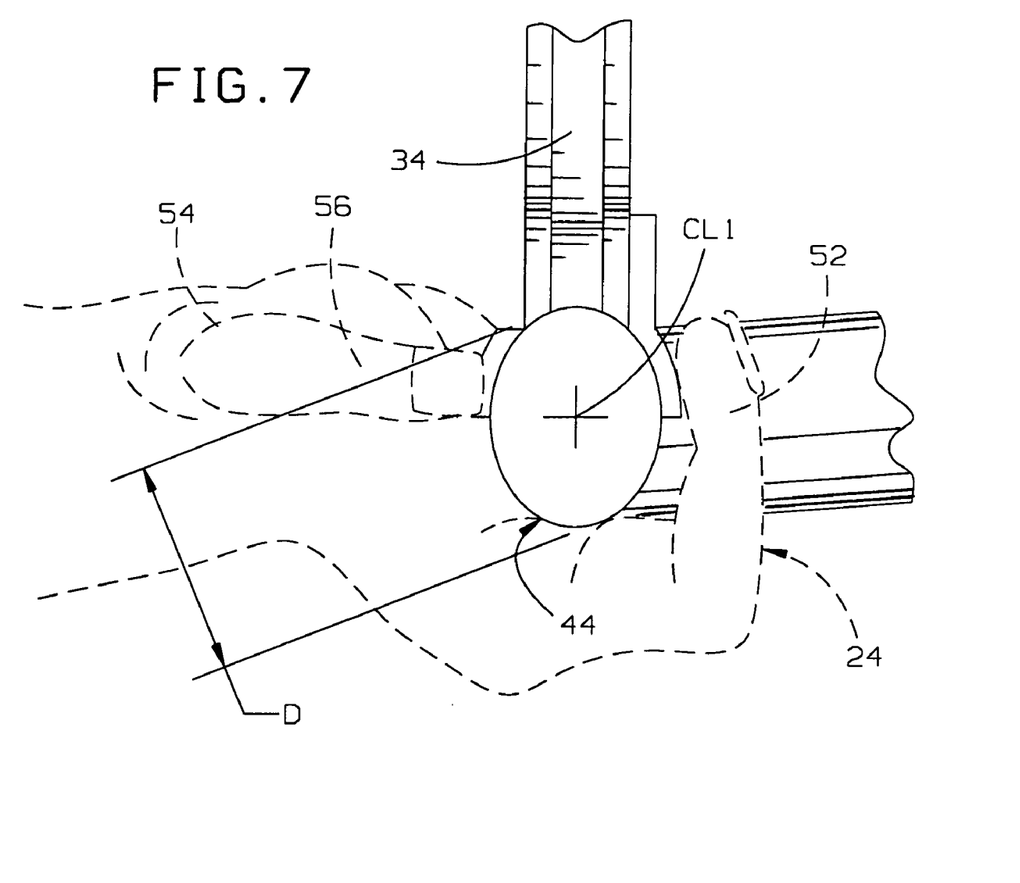
FIG. 7 is an enlarged, fragmentary, plan view of a portion of the housing assembly in FIGS. 3-6 gripped by the hand of a user.

The peripheral surface 50 is configured to be graspable operatively between a) at least one, and preferably a plurality, of the user's fingers 52 and b) a palm 54 and/or thumb 56 on the same hand 24. With this arrangement, the contour 44 can be squeezed so as to bear the palm 54 and/or thumb 56 under pressure into operative contact with the front electrode 20a and the finger(s) 52 into operative contact with the rear electrode 20b. The user's left hand 22 grasps the contour 42 and operatively contacts the electrodes 20a, 20b under pressure in like manner so that an electrical impulse from the generator 26 can be imparted to the user's right hand 24 to pass through the user's body to the left hand 22 and to the electrodes 18a, 18b. Based on this transmission, the impedance sensor signal generator 28, 28' generates an impedance signal indicative of the user's body composition.

To facilitate comfortable wrapping of the user's hands, 22, 24 around the contours 42, 44, the exemplary surface 50 is made with a convex shape extending through preferably in excess of 180° around the center line (CL1) for the exemplary contour 44 that is shown to be non-orthogonal to the support surface 38 that resides in the aforementioned reference plane. With this shape, the contours 42, 44 can be firmly operatively gripped, whereby the user's hands are brought firmly into operative contact with the electrodes 18a, 18b, 20a, 20b. The ends of the users fingers 52 are allowed to conveniently nest in a receptacle 58 defined jointly by the upright wall 34 and transverse base 36.

Ideally, the housing assembly 16 has a relatively compact configuration. To minimize the required footprint on the subjacent support surface 38, the electrodes 18a, 18b, 20a, 20b are made with an elongate shape aligned in a vertical direction. Also with this arrangement, the user 10 is allowed to operatively grip the contours 42, 44 and operatively contact the electrodes 18a, 18b, 20a, 20b with the hands 22, 24 in an ergonomically comfortable position in which they naturally rest, as with the user sitting in a chair at a desk. The gripping action is similar to that used by a driver to grip a steering wheel on a vehicle, albeit with the hands closer together.

Figure 3:
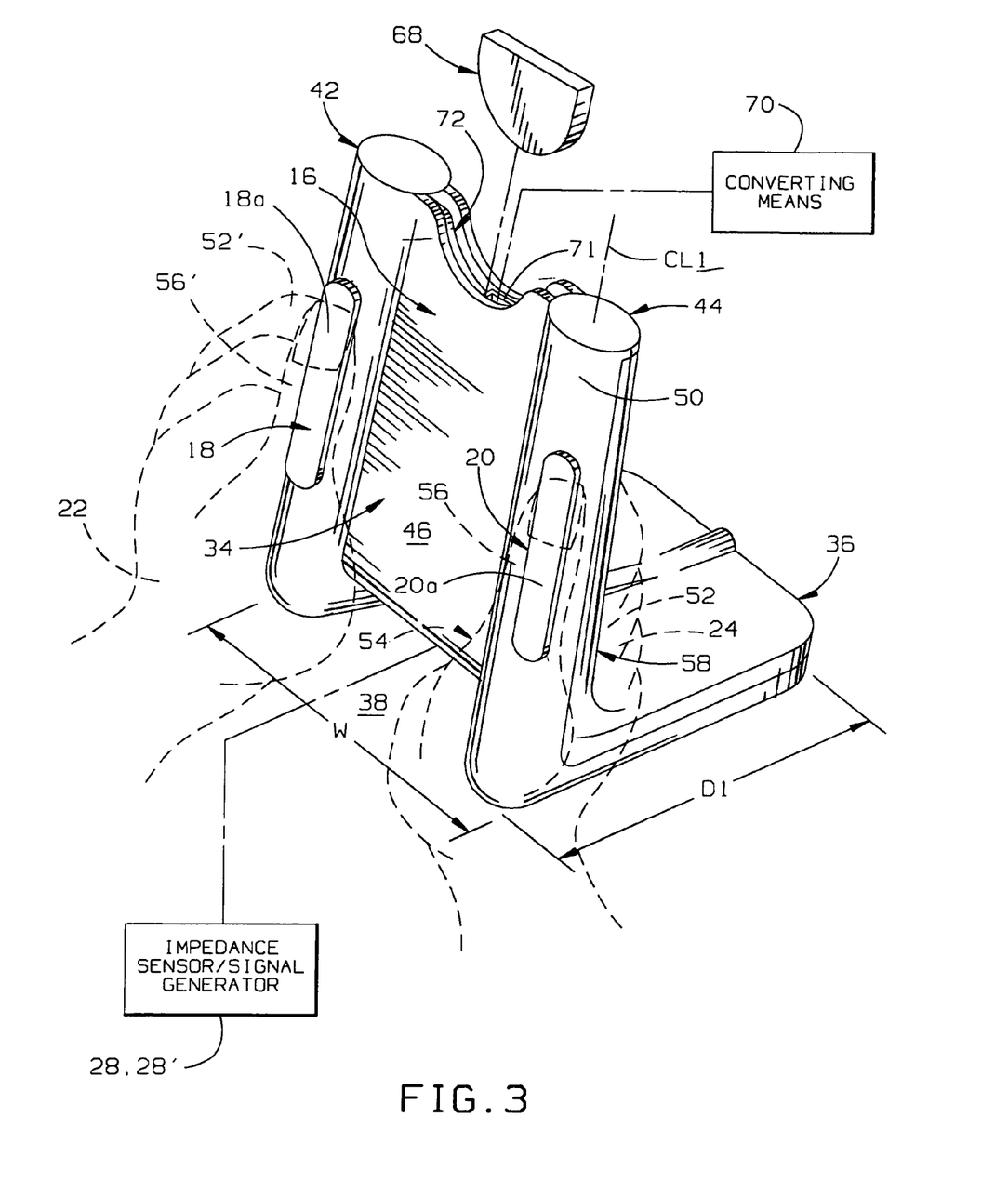
FIG. 3 is a front perspective view of a housing assembly on the systems in FIGS. 1 and 2, additionally showing an independently operable device separated from a docking station on the housing assembly.
Figures 4, 5:
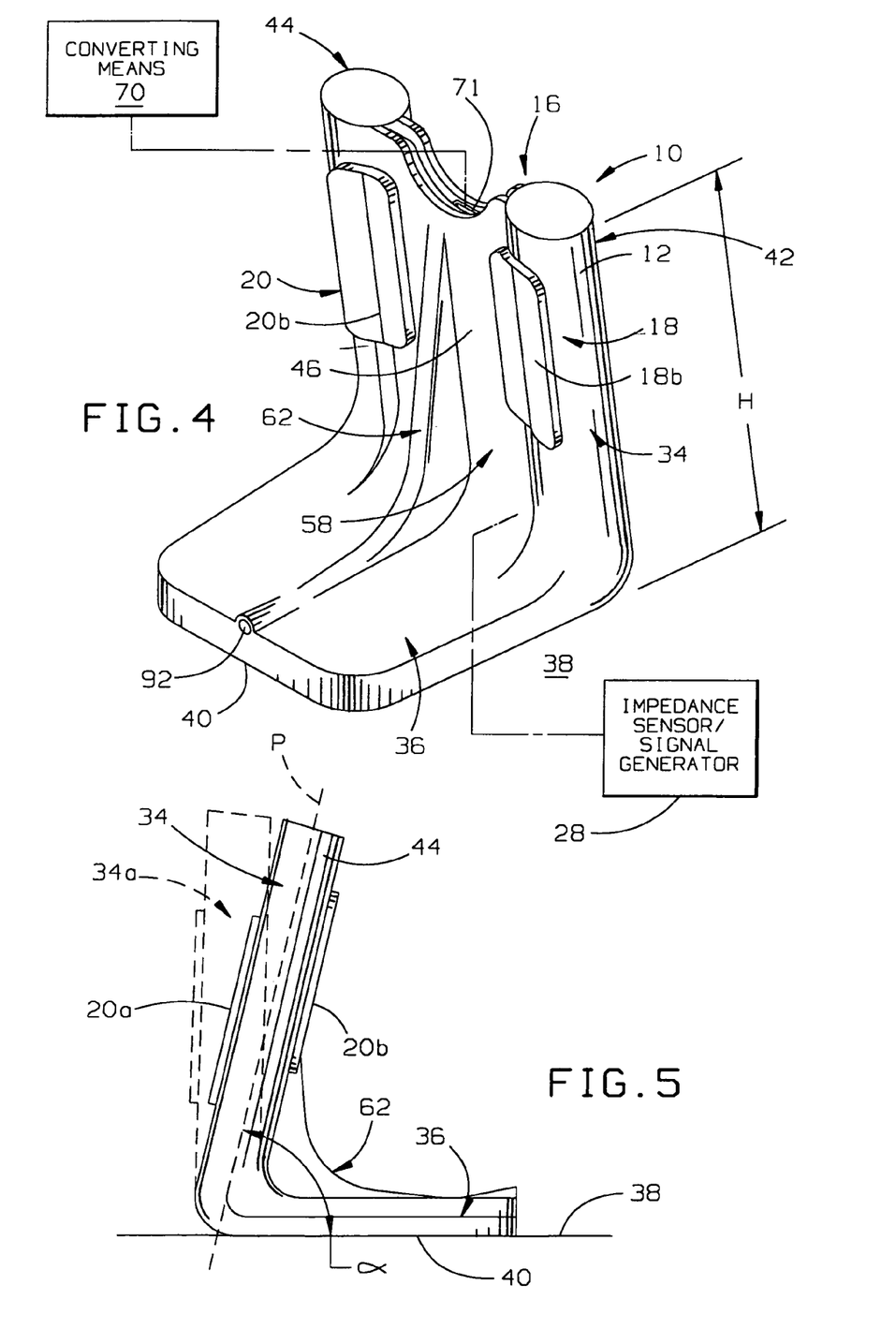
FIG. 4 is a rear perspective view of the housing assembly in FIG. 3.
FIG. 5 is a side elevation view of the housing assembly in FIG. 4.
Figure 6:
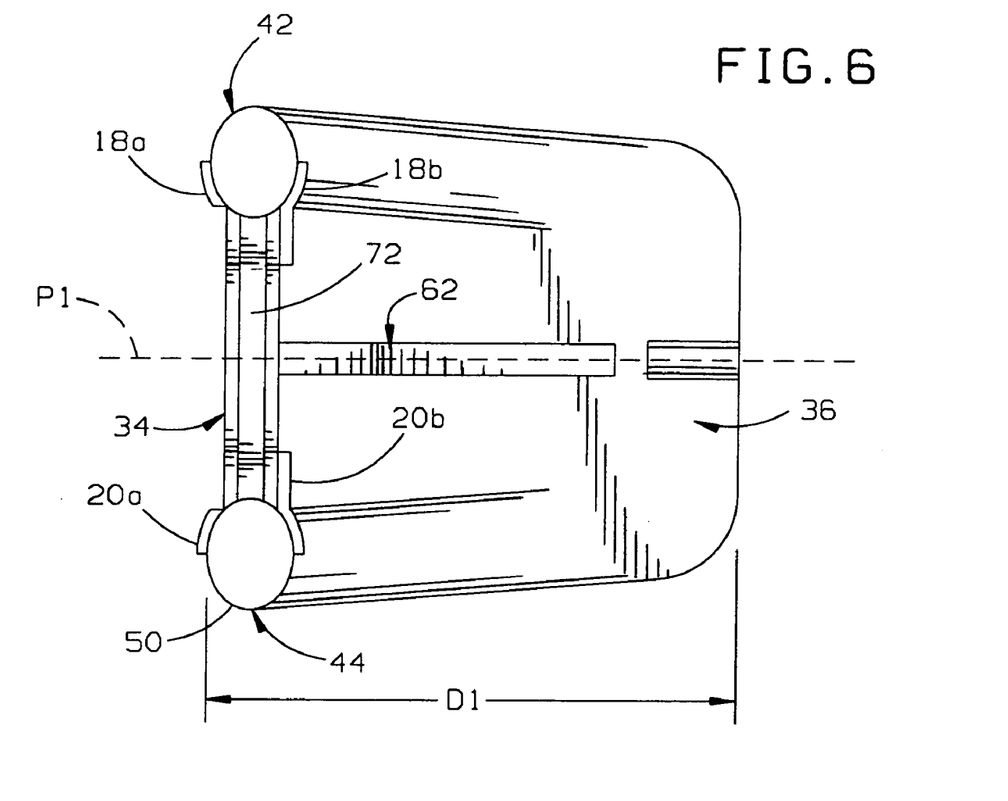
FIG. 6 is a plan view of the housing assembly in FIGS. 3-5.

As can be seen, with the housing assembly 16 operatively grasped by the user, the user's thumbs 56, 56' extend vertically in generally lengthwise alignment with the lengthwise extent of the contours 42, 44. With this arrangement, the thumbs 56, 56' can be brought into contact with the electrodes 18a, 20a at the front of the housing assembly 16 in relatively close proximity, without the fear of inadvertent contact between the thumbs 56, 56' on the opposite hands 22, 24 as would preclude the generation of a meaningful impedance signal. Consequently, the upright wall 34 can be made with a relatively narrow width W (FIG. 3).

Figure 8:
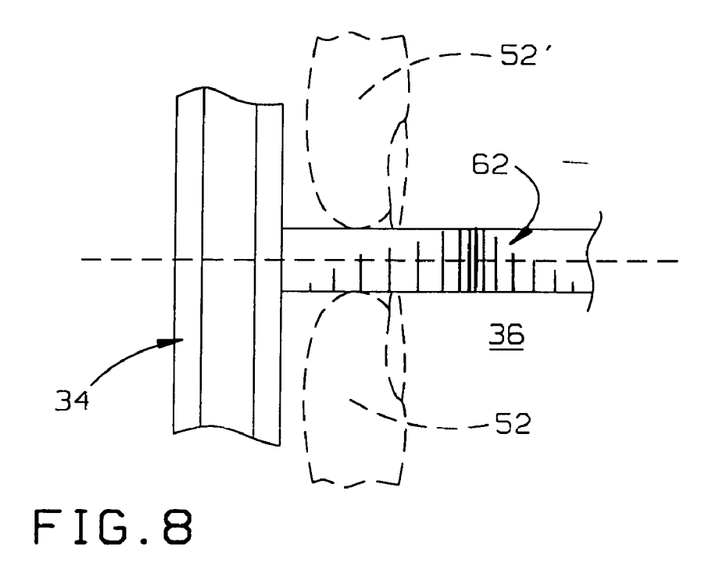
FIG. 8 is an enlarged, fragmentary, plan view of an insulating barrier assembly on the housing assembly in FIGS. 3-7 in relationship to a user's fingers on separate hands wrapped around the housing assembly.

Since the fingers 52, 52' wrap and extend in a more horizontal orientation around the contours 42, 44, there is the potential that the fingers 52, 52' on the user's separate hands 22, 24 might inadvertently contact each other at the back of the upright wall 34, in a region where they reside between the upright wall 34 and base 36 with the contours 42, 44 operatively gripped. To avoid inadvertent contact between the fingers 52, 52' on the user's separate hands, an electrically insulating barrier assembly at 62 is incorporated at the rear of the upright wall 34. The barrier assembly 62 resides in the region at which the fingers 52, 52' converge as the hands 22, 24 grip the contours 44, 42. The barrier assembly 62 may be in the form of a solid wall or a membrane made from plastic, rubber, or other suitable insulating material, and located midway between the contours 42, 44.

By reason of including the barrier assembly 62, the width dimension W of the upright wall 34 can be maintained at a relatively small dimension. Ideally, the width W is less than six (6) inches, and more preferably on the order of four (4) inches or less. A fore-and-aft dimension D1 can be selected to stably support the housing assembly 16 in the operative orientation. Typically, the dimension D will be on the order of six (6) inches or less. The height H (FIG. 4) of the upright wall 34 likewise is on the order of six (6) inches or less.

The housing assembly 16 is shown in combination with an independently operable device at 68. In this embodiment, the device 68 is an activity monitor of the type sold by the assignee herein commercially under the trademark CT1. The device 68 is capable of recording the burning of calories over prescribed periods of activity. The device 68 is downloaded using a converting means 70. Typically, the device 68 will be worn on the user to take measurements. Once the activity period for which readings are sought is concluded, the device 68 can be placed at the top of the upright wall 34. An electrical connector/port element in the form of a mini USB connector 71 may be provided in a receptacle 72 to communicate with the converting means 70. The housing assembly 16 thereby functions as a docking station for the device 68. The converting means 70 may be integral with the housing assembly 16 or separate therefrom and may take any form appropriate to convert the stored data in the device 68 to a useable form.

Figure 9:
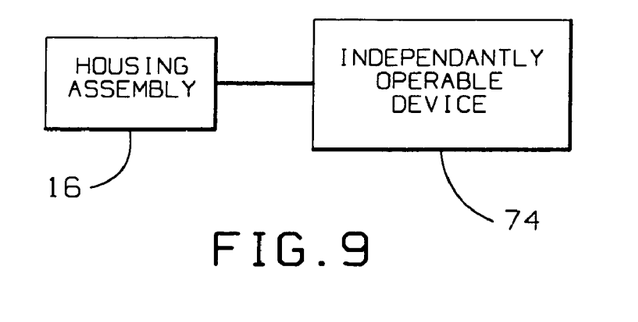
FIG. 9 is a schematic representation of the inventive housing assembly associated with an independently operable device.

The invention contemplates using the housing assembly 16 as a support to releasably store virtually any type of independently operable device 74, as shown in FIG. 9. As just one example, the device 74 may be a desk accessory. The desk accessory may be in the nature of a container for commonly used desk items, or the like, or may be independently operated as, or integrated into, a functional item. The function performed by the device 74 may be primarily aesthetic in nature. This allows the housing assembly 16 to be multi-functional and to blend into a particular environment in which it is used. The device 74 may be integral with the housing assembly 16 or separate and integrated thereinto.

The system 12 may be used to develop different signals indicative of a state of a user's body. In a preferred form, an impedance signal is generated from which at least one of a user's percentage of a) body water, b) body fat, and c) lean muscle mass can be measured and ascertained. With the compact construction of the housing assembly 16, the user can maintain the same in a convenient location to be readily accessed for a quick measurement, as at a desk or workstation. This facilitates regular, ongoing monitoring of a particular health-related attribute, such as body composition.

Figures 10, 11, 12:
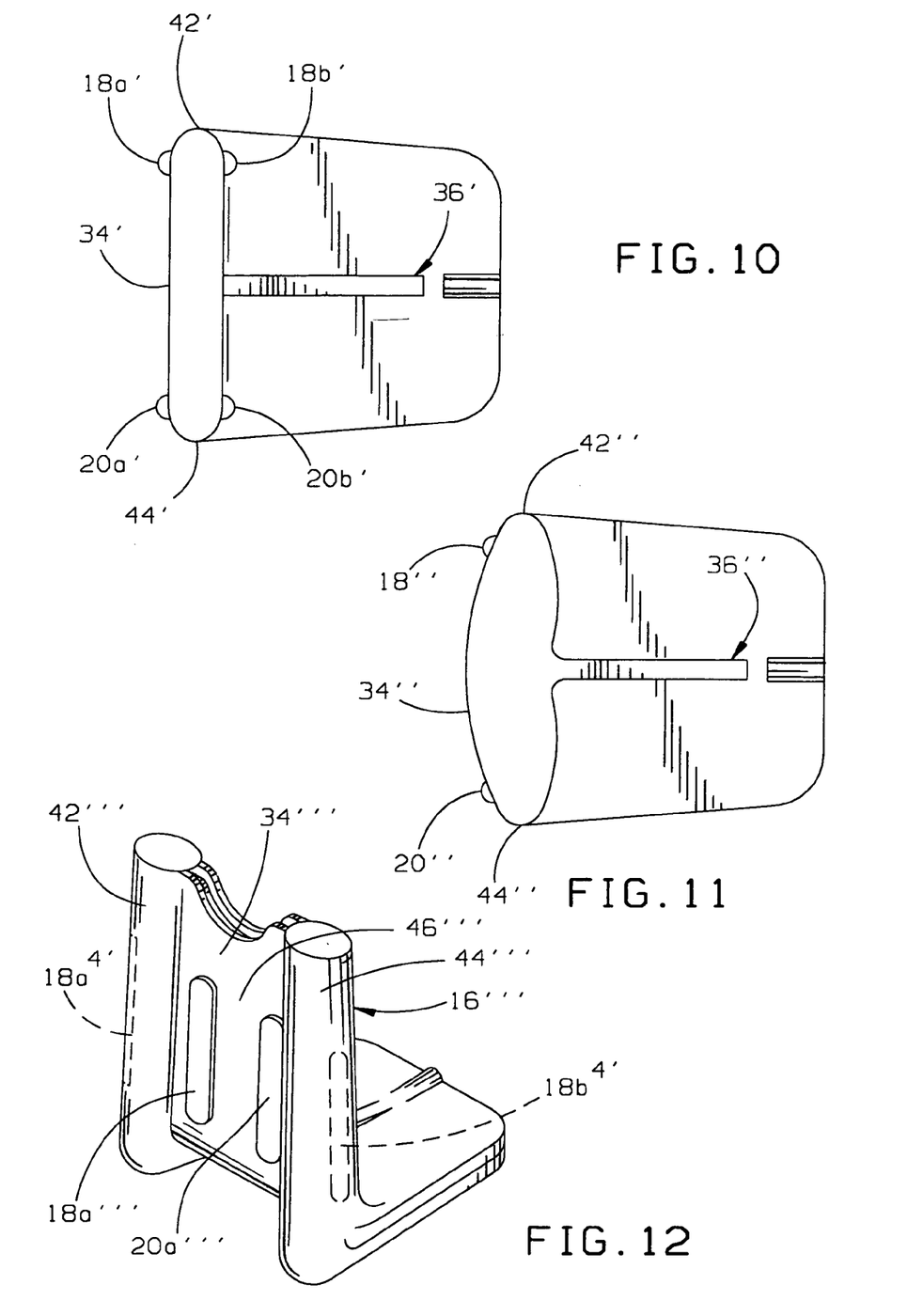
FIG. 10 is a view as in FIG. 6 of a modified form of housing assembly.
FIG. 11 is a view as in FIG. 6 of a further modified form of housing assembly.
FIG. 12 is a view corresponding to that in FIG. 3 of a modified form of housing assembly wherein electrodes are placed in different positions on the housing assembly.

Various modifications to the system 12 are contemplated. For example, as shown in FIG. 10, the upright wall 34' may have a different configuration, including that for the contours 42', 44', on which electrodes 18$a'$, 18$b'$, 20$a'$, 20$b'$ are provided. In this embodiment, the contours 42', 44' blend together without a discrete web region, corresponding to the web 46. The upright wall 34' projects from a base 36'.

A virtually limitless number of different shapes can be arrived at to provide an upright wall that is graspable to operatively contact separate electrodes. As just one further example, as shown in FIG. 11, the upright wall 34" has a generally elliptical or kidney shape on which the contours 42", 44" are provided. A single electrode 18", 20" is provided on each contour 42", 44". The upright wall 34" projects from a base 36".

Essentially, what is significant and desirable is that the upright wall 34, 34', 34" be conveniently graspable to bear the user's hands 22, 24 under pressure positively against the electrodes 18$a$, 18$a'$, 18", 18$a'''$, 18$b$, 18$b'$, 20$a$, 20$a'$, 20", 20$b$, 20$b'$. The precise shape of the upright wall 34, 34$a$, 34' 34" or associated contours is not critical to the present invention.

In another variation, as shown in FIG. 12, a housing assembly 16''' has electrodes 18$a'''$, 20$a'''$ located on a web 46''' adjacent to contours 42''', 44''' which are grasped by a user during operation. The user's palm and thumb regions can be operatively contacted with the electrodes 18$a'''$, 20$a'''$ using the aforementioned gripping action. Electrodes (not shown) may be provided at the rear of the upright wall 34''' to be paired with the electrodes 18$a'''$, 20$a'''$.

The invention also contemplates that but a single electrode could be provided to be operatively contacted by each hand of the user. An electrode on each contour 42, 42', 42", 42''', 44, 44', 44", 44''' could be located as described hereinabove or elsewhere, such as the electrodes 18$a^{4'}$, 20$a^{4'}$, as shown in dotted lines in FIG. 12. The electrodes, to be used in each pair, can be at the front and rear, front and side, rear and side, etc. Electrodes can be provided in groups of three or more at each contour. The shape of each electrode can vary from what is described hereinabove. The critical objective, regardless of the shape, number, size, and location of the electrodes, is to provide electrodes that can be positively operatively contacted to permit accurate measurement, such as the bio-impedance measurement, preferably using a comfortable gripping action.

The invention also contemplates that the contours 42, 44 could be grasped other than as described above, as by other appendages.

Figure 13:
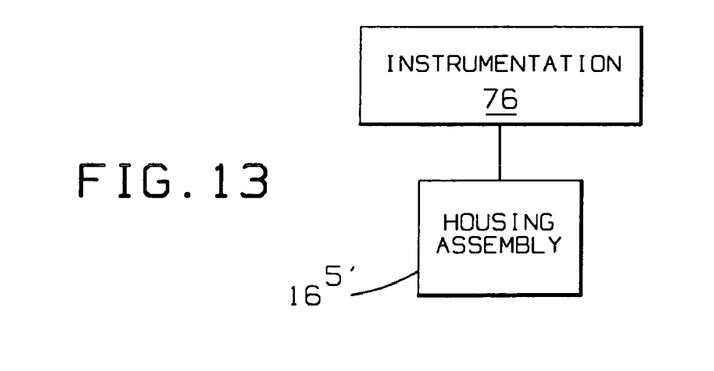
FIG. 13 is a schematic representation of a generic form of the inventive system for generating a signal indicative of a state of a user's body.

The invention contemplates that the housing assembly 16$^{5'}$ could be used to take other measurements through appropriate instrumentation 76, as shown in FIG. 13. The instrumentation 76 may take a user's pulse, collect data relative to a user's response to activity, or measure any other body characterization or function, and generate a signal indicative thereof.

The general operation of the subsystem 14, designed as a bio-impedance measuring device, to determine body water, body fat and lean muscle mass percentages, will now be described. The impulse generator 26 transmits a low power, electrical signal through the body of a user. One electrode pair 18, 20 transmits an electrical signal, while the other pair 18, 20 receives the electrical signal, after it passes through the body of the user. From the impedance data processed by the sensor/signal generator 28, body water, body fat and lean muscle mass percentages may be determined for the user. This may be done using stand alone technology or using data from an existing data base and a web server.

The subsystem 14 may be a self-contained unit capable of generating human readable data relative to body composition. Preferably, the subsystem 14 utilizes a low power and low cost microprocessor, with intensive processing performed at the signal converting means 30, which may be a web server or other suitable instrumentation. This avoids the need for costly, high powered microprocessors in the subsystem 14. This is known as a thin-client processing model. The thin-client processing architecture of the invention enables the device to be significantly cost reduced. Other "intelligent" monitoring instruments with rich user interface may require complicated and expensive microprocessors and display circuitry.

Another benefit of the thin-client processing architecture includes easy implementation of instrument software upgrades. Standard monitoring instruments generally must be sent to a service facility for a hardware or software upgrade, thus placing an inconvenience and cost burden on the user. Software upgrades for the inventive device simply require modifying software access flags within the centralized database software, essentially removing the need for a service event. The benefits of periodic software upgrades include additional functionality, improved accuracy, and/or the post purchase enabling of exclusive features unavailable at the time of purchase.

As noted above, the electrodes 18$a$, 18$b$, 20$a$, 20$b$ are the elements of the subsystem 14 that are operatively contacted by the user in order to send and receive the electrical impulse. A bio-impedance based body composition measurement utilizes a body conductance model that typifies ionic current flow within human tissue. One such model is the Cole-Cole method that models ionic current flows in human tissue as a resistor in parallel with a resistor and capacitor in series. This model considers the intracellular current and extracellular fluid current flow. In the Cole-Cole model, the cellular wall is modeled as an electronic capacitor, as an energy storage mechanism that tends to store electrical charge. Using this model requires a circuit sensitive enough to measure the tissue capacitance due to the cellular walls. A problem potentially exists if the capacitance variability between the skin and many types of electrodes is far greater than the capacitance of the cellular wall, thereby making it impossible to measure the small intracellular capacitance. To circumvent this problem, the electrodes 18a, 18b, 20a, 20b may each include a surface area with a plurality of conductive fibers embedded. The conductive fibers reduce skin-to-electrode capacitance by increasing direct contact between the electrodes 18a, 18b, 20a, 20b and the user, which ultimately enables the use of capacitive tissue models when measuring bio-impedance.

By reason of the configuration of the housing assembly 16, the user is permitted to operatively contact the electrodes 18, 20 with the arms and hands extended naturally straight with little tension therein. Muscle tension during bio-impedance measurement has shown to influence body composition measurement. This is especially true in the arms due to the prevalence of lean muscle mass, or more specifically, because the arms are relatively high impedance with respect to the torso region.

The subsystem 14 may communicate with a computer device with access to a network database used in conjunction with the bio-impedance measuring device. In a preferred embodiment, the database is one part of a website. The computer device is not restricted to a specific means of accessing the internet, so long as programs running in conjunction with the bio-impedance measuring device on the computer device can access the internet.

Figure 14:
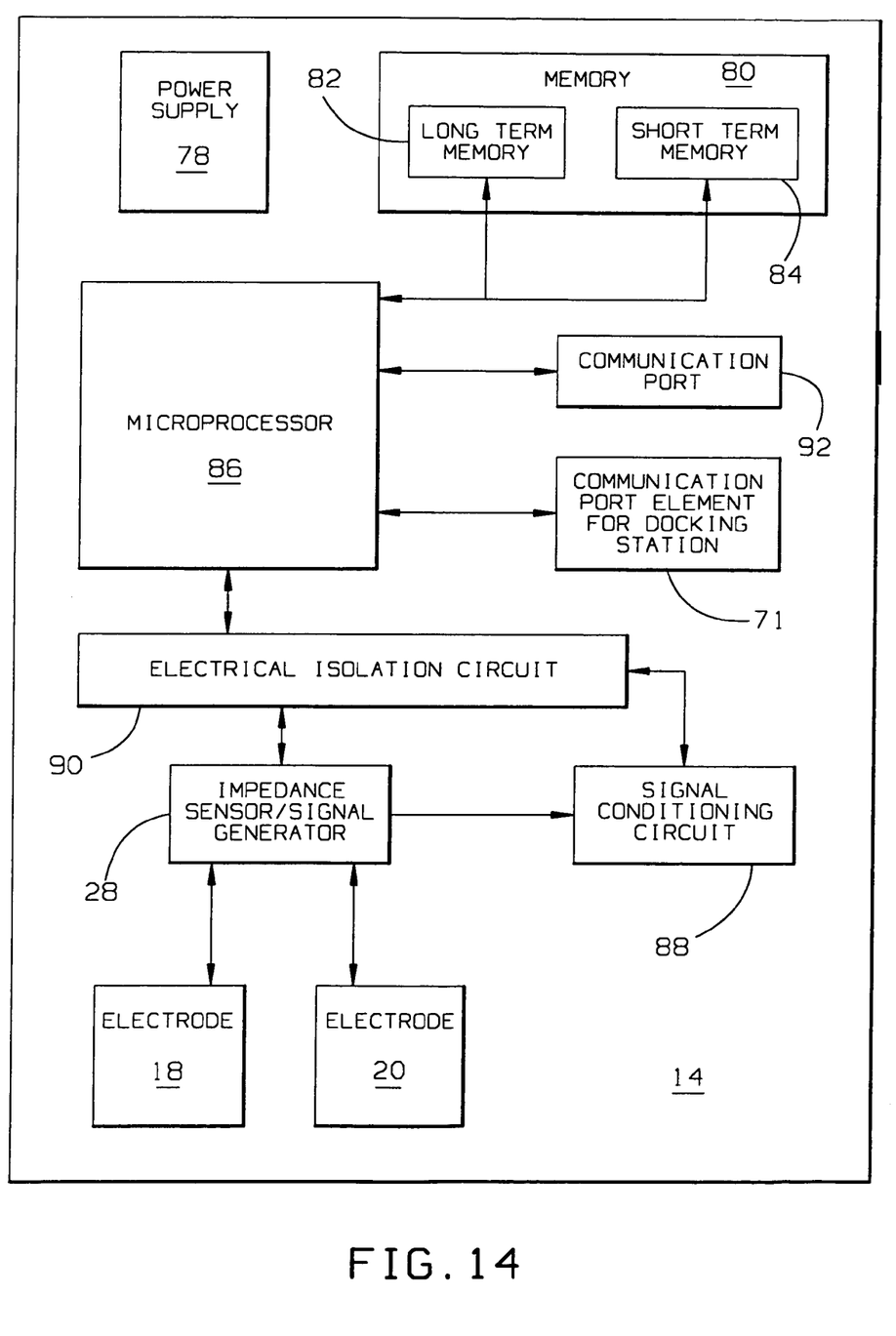
FIG. 14 is a schematic representation of internal system components on one form of the inventive housing assembly.

In FIG. 14, internal components of one exemplary form of bio-impedance measuring subsystem 14 are shown. This is not intended to be limiting, nor is the invention limited to bio-impedance measuring. The elements include a power supply 78, memory 80, consisting of long term memory 82 and short term memory 84, microprocessor 86, the impedance sensor/signal generator 28, signal conditioning circuit 88, electrical isolation circuit 90, communication port 92 (FIG. 4), and the communication port element 71 for the receptacle 72 defining the docking station.

The power supply 78 converts battery power to the necessary voltage and current requirements for the various sub-circuits. The power supply 78 provides power to all of the electrical components. Additionally, a preferred embodiment of the invention includes a power supply that can switch voltage levels and current amplitudes efficiently in order to optimize power conversion and reduce energy losses which are associated with other power supplies. This ultimately conserves battery power and extends the battery life of the subsystem 14. Furthermore, the power supply 78 may utilize an isolation transformer (a transformer with a 1:1 turn ratio) as opposed to a standard coil in the power supply switching circuit embodiments in the invention. This enables a single component, the isolation transformer, to serve the dual purpose of the energy storage function of the primary coil and a secondary coil to transfer energy to the electrically isolated elements of the subsystem 14.

As seen in FIG. 14, the memory 80 consists of the long term memory 82 (non-volatile memory) and short term memory 84 (volatile memory). In a preferred embodiment of the invention, the long term memory 82 stores bio-impedance measuring device related information (i.e. serial number, model number, calibration data, etc.) and personal information (height, gender, etc.). This information is preferably programmed into the device during manufacturing in a user configuration session.

The subsystem 14 utilizes the short term memory 84 to store less critical information, such as logged data and electrical impulse processing data. In a preferred form, the short term memory 84 is large enough to maintain several days of user data. After this time period, the data may be overwritten. The short term memory 84 may be purged of user data after transferring the same.

The microprocessor 86 is configured to process an impedance signal from the impedance sensor/signal generator 28, data from the communication port 92, and data from the communication port element/connector 71 of the receptacle 72 at the docking station. The impedance sensor/signal generator 28 is coupled with the electrode pairs 18, 20 and measures impedance using well known techniques. Prior to reaching the microprocessor 86, the impedance signal (small signal) from the impedance sensor/signal generator 28 is filtered and amplified by the signal conditioning circuit 88 using well known techniques. These two steps insure that the impedance signal is properly scaled and conditioned for standard, digital-to-analog converters included in the subsystem 14.

The electrical isolation circuit 90 provides electrical isolation between the user of the subsystem 14 and various subcircuits. This reduces the possibility of a user being shocked. As noted above, the subsystem 14 is designed to send an electrical impulse to the body of a user. The conductive pathway for this impulse through the bio-impedance measuring device also provides a path for high levels of energy during a failure encountered in the system.

The foregoing disclosure of specific embodiments is intended to be illustrative of the broad concepts comprehended by the invention.

The invention claimed is:

1. A system for generating a signal indicative of a state of a user's body, the system comprising:

a housing assembly; and first and second spaced electrodes on the housing assembly situated so that an electrical impulse can be generated a) through the first electrode to a first user appendage in operative contact with the first electrode and b) from a second user appendage in operative contact with the second electrode to the second electrode, to thereby allow generation of a user impedance signal, the user impedance signal usable to identify a state of a user's body, wherein the housing assembly has first and second contours that can be operatively grasped, one each in the hand of a user so that the fingers on the user's hands converge towards each other and as to allow each hand to operatively contact one of the electrodes while avoiding direct contact between the hands grasping the first and second contours, wherein the first electrode is on the first contour, the system further comprising a third electrode on the first contour that is electrically insulated from the first electrode, the first and third electrodes facing oppositely and situated so that a user's one hand can grasp the first contour and thereby the first and third electrodes with a squeezing action so that the first electrode is pressed forcibly against at least one of the user's fingers on the user's one hand and the third electrode is pressed forcibly against the palm and/or thumb on the user's one hand, the second contour graspable by the user's other hand to cause the signal indicative of a state of the user's body to be generated, the housing assembly configured so that with the user's one hand grasping the first contour the user's at least one finger on the one hand against which the first electrode is pressed is blocked by the housing assembly from contacting the user's palm and/or thumb on the one hand against which the third electrode is pressed, wherein the housing assembly has an electrically insulating barrier assembly at a region between the first and second contours where the user's fingers converge with the user's hands operatively grasping the first and second contours to engage a user's finger tips and thereby block inadvertent contact between fingers on the user's one hand with fingers on the user's other hand.

2. The system for generating a signal indicative of a state of a user's body according to claim 1 wherein the first contour comprises a surface curved convexly through in excess of 180° around a centerline for the first contour and around which a user's fingers on the one hand can be wrapped with the user's one hand in operative contact with the first electrode.

3. The system for generating a signal indicative of a state of a user's body according to claim 1 wherein the housing assembly has a front and rear and the first electrode is on only one of the front and rear of the housing.

4. The system for generating a signal indicative of a state of a user's body according to claim 3 wherein the third electrode on only the other of the front and rear of the housing.

5. A system for generating a signal indicative of a state of a user's body, the system comprising:

a housing assembly; and first and second spaced electrodes on the housing assembly situated so that an electrical impulse can be generated a) through the first electrode to a first user appendage in operative contact with the first electrode and b) from a second user appendage in operative contact with the second electrode to the second electrode, to thereby allow generation of a user impedance signal, the user impedance signal usable to identify a state of a user's body, wherein the housing assembly has an electrically insulating barrier assembly defined between first and second contours on the housing assembly at or adjacent to which the first and second electrodes are respectively located, the insulating barrier assembly residing between first and second user appendages in operative contact with the first and second electrodes so as to block direct contact between the first and second user appendages, wherein the housing assembly comprises an upright wall and a transverse base, the first and second electrodes are on the upright wall and the transverse base defines a surface to bear on a subjacent support to maintain the housing assembly in an operative orientation, at least one of the user appendages in operative contact with the first electrode residing in a region between the upright wall and transverse base.

6. The system for generating a signal indicative of a state of a user's body according to claim 5 wherein the housing assembly has a front and rear and spaced sides and the upright wall and transverse base define one of an "L" or a "U" shape as viewed from the side of the housing assembly.

7. The system for generating a signal indicative of a state of a user's body according to claim 1 wherein the first contour has a convexly curved surface.

8. The system for generating a signal indicative of a state of a user's body according to claim 7 wherein the convexly curved surface has an effective diameter of not greater than two (2) inches.

9. The system for generating a signal indicative of a state of a user's body according to claim 7 wherein the convexly curved surface extends through in excess of 180° around a centerline for the curved surface.

10. The system for generating a signal indicative of a state of a user's body according to claim 1 further comprising a generator for an electrical impulse on the housing assembly to be directed through the first electrode.

11. The system for generating a signal indicative of a state of a user's body according to claim 1 further comprising a generator for the user impedance signal on the housing assembly.

12. The system for generating a signal indicative of a state of a user's body according to claim 1 further in combination with a means for converting the user impedance signal to a human readable form.

13. The system for generating a signal indicative of a state of a user's body according to claim 12 wherein the converting means converts the user impedance signal to a measurement that is at least one of a user's percentage of a) body water, b) body fat, and c) lean muscle mass.

14. A system for generating a signal indicative of a state of a user's body, the system comprising:

a housing assembly; and first and second spaced electrodes on the housing assembly situated so that an electrical impulse can be generated a) through the first electrode to a first user appendage in operative contact with the first electrode and b) from a second user appendage in operative contact with the second electrode to the second electrode, to thereby allow generation of a user impedance signal, the user impedance signal usable to identify a state of a user's body, wherein the housing assembly has an electrically insulating barrier assembly defined between first and second discrete contours on the housing assembly at or adjacent to which the first and second electrodes are respectively located, the insulating barrier assembly residing between first and second user appendages in operative contact with the first and second electrodes so as to engage at least a part of the first user appendage and thereby block direct contact between the first and second user appendages, the system provided in combination with a means for converting the user impedance signal to a human readable form, wherein the converting means comprises at least one of a personal computer and a web server, that is separate from the housing assembly.

15. A system for generating a signal indicative of a state of a user's body, the system comprising:

a housing assembly; and first and second spaced electrodes on the housing assembly situated so that an electrical impulse can be generated a) through the first electrode to a first user appendage in operative contact with the first electrode and b) from a second user appendage in operative contact with the second electrode to the second electrode, to thereby allow generation of a user impedance signal, the user impedance signal usable to identify a state of a user's body, wherein the housing assembly has an electrically insulating barrier assembly defined between first and second contours on the housing assembly at or adjacent to which the first and second electrodes are respectively located, the insulating barrier assembly residing between first and second user appendages in operative contact with the first and second electrodes so as to block direct contact between the first and second user appendages, the system provided in combination with an independently operable device that is mounted to the housing assembly to thereby be releasably stored on the housing assembly.

16. The system for generating a signal indicative of a state of a user's body according to claim 15 wherein the system defines a docking station for the independently operable device that is an instrument to measure a health-related attribute of a user.

17. The system for generating a signal indicative of a state of a user's body according to claim 15 wherein the independently operable device is a desk accessory.

18. A system for generating a signal indicative of a state of a user's body, the system comprising:

a housing assembly;

first and second spaced electrodes on the housing assembly situated so that an electrical impulse can be generated a) through the first electrode to a first user appendage in operative contact with the first electrode and b) from a second user appendage in operative contact with the second electrode to the second electrode, to thereby allow generation of a user impedance signal, the user impedance signal usable to identify a state of a user's body, wherein the housing assembly has first and second contours that can be operatively grasped, one each in the hand of a user, so as to allow each hand to operatively contact one of the electrodes while avoiding direct contact between the hands operatively grasping the first and second contours, the first hand gripping the first electrode wrapping around a center line of the first contour; and a base for supporting the housing assembly consistently in an operative orientation relative to a flat surface residing in a reference plane in which operative orientation the first and second electrodes can be operatively grasped while using the system, wherein the center line of the first contour is non-orthogonal to the reference plane.

19. The system for generating a signal indicative of a state of a user's body according to claim 18 wherein the first and second contours comprise discrete first and second contours.

20. The system for generating a signal indicative of a state of a user's body according to claim 18 wherein the first contour comprises a surface around which a user's fingers on one hand can be wrapped with the user's one hand in operative contact with the first electrode.

21. The system for generating a signal indicative of a state of a user's body according to claim 18 wherein the first contour is configured to be graspable operatively between a) a finger and b) the palm and/or thumb on a hand of a user.

22. The system for generating a signal indicative of a state of a user's body according to claim 18 wherein the housing assembly has a front and rear and the first electrode is on one of the front and rear of the housing.

23. The system for generating a signal indicative of a state of a user's body according to claim 22 wherein there is a third electrode on the other of the front and rear of the housing and the first discrete contour is configured to be graspable operatively between the a) fingers and b) palm and/or thumb on a hand of a user.

24. The system for generating a signal indicative of a state of a user's body according to claim 23 wherein the first and third electrodes are electrically insulated from each other and with a user operatively grasping the first discrete contour, the first electrode is operatively contacted by at least one of a user's fingers and the third electrode is operatively contacted by a user's palm and/or thumb.

25. The system for generating a signal indicative of a state of a user's body according to claim 18 wherein the first electrode is located to be operatively contacted by one of a) the palm and/or thumb and b) at least one finger on a hand that is operatively grasping the first contour.

26. A system for generating a signal indicative of a state of a user's body, the system comprising:

a housing assembly; and first and second spaced electrodes on the housing assembly situated so that an electrical impulse can be generated a) through the first electrode to a first user appendage in operative contact with the first electrode and b) from a second user appendage in operative contact with the second electrode to the second electrode, to thereby allow generation of a user impedance signal, the user impedance signal usable to identify a state of a user's body, wherein the housing assembly has first and second contours that can be operatively grasped, one each in the hand of a user, so as to allow each hand to operatively contact one of the electrodes while avoiding direct contact between the hands operatively grasping the first and second contours, wherein the housing assembly comprises an upright wall and a transverse base, the first and second electrodes are on the upright wall and the transverse base defines a surface to bear on a subjacent support to maintain the housing assembly in an operative orientation, the user's fingers operatively grasping the first and second contours residing on a region between the upright wall and transverse base.

27. The system for generating a signal indicative of a state of a user's body according to claim 26 wherein the housing assembly has a front and rear and spaced sides and the upright wall and transverse base define one of an "L" or a "U" shape as viewed from the side of the housing assembly.

28. The system for generating a signal indicative of a state of a user's body according to claim 18 wherein the first contour has a convexly curved surface.

29. The system for generating a signal indicative of a state of a user's body according to claim 28 wherein the convexly curved surface has an effective diameter of not greater than two (2) inches.

30. The system for generating a signal indicative of a state of a user's body according to claim 28 wherein the convexly curved surface extends through in excess of 180° around a centerline for the curved surface.

31. The system for generating a signal indicative of a state of a user's body according to claim 18 further comprising a generator for an electrical impulse on the housing assembly to be directed through the first electrode.

32. The system for generating a signal indicative of a state of a user's body according to claim 18 further comprising a generator for the user impedance signal on the housing assembly.

33. The system for generating a signal indicative of a state of a user's body according to claim 18 further in combination with a means for converting the user impedance signal to a human readable form.

34. The system for generating a signal indicative of a state of a user's body according to claim 33 wherein the converting means converts the user impedance signal to a measurement that is at least one of a user's percentage of a) body water, b) body fat, and c) lean muscle mass.

35. A system for generating a signal indicative of a state of a user's body, the system comprising:
  a housing assembly comprising an upright wall and a transverse base; and
  first and second spaced electrodes on the upright wall on the housing assembly situated so that an electrical impulse can be generated a) through the first electrode to a first user appendage in operative contact with the first electrode and b) from a second user appendage in operative contact with the second electrode to the second electrode, to thereby allow generation of a user impedance signal,
  the user impedance signal usable to identify a state of a users body,
  wherein the housing assembly has first and second contours that can be operatively grasped, one each in the hand of a user, so as to allow each hand to operatively contact one of the electrodes while avoiding direct contact between the hands operatively grasping the first and second contours,
  at least one of the user appendages in operative contact with the first electrode residing in a region between the upright wall and transverse base,
  the system provided in combination with a means for converting the user impedance signal to a human readable form,
  wherein the converting means comprises at least one of a personal computer and a web server that is separate from the housing assembly.

36. A system for generating a signal indicative of a state of a user's body, the system comprising:
  a housing assembly; and
  first and second spaced electrodes on the housing assembly situated so that an electrical impulse can be generated a) through the first electrode to a first user appendage in operative contact with the first electrode and b) from a second user appendage in operative contact with the second electrode to the second electrode, to thereby allow generation of a user impedance signal,
  the user impedance signal usable to identify a state of a user's body,
  wherein the housing assembly has first and second contours that can be operatively grasped, one each in the hand of a user, so as to allow each hand to operatively contact one of the electrodes while avoiding direct contact between the hands operatively grasping the first and second contours,
  the system provided in combination with an independently operable device that is separately mounted to the housing assembly to thereby be releasably stored upon the housing assembly.

37. The system for generating a signal indicative of a state of a user's body according to claim 36 wherein the system defines a docking station for an independently operable device that is an instrument to measure a health-related attribute of a user.

38. The system for generating a signal indicative of a state of a user's body according to claim 37 wherein the independently operable device is a desk accessory.

39. The system for generating a signal indicative of a state of a user's body according to claim 18 wherein the housing assembly comprises an electrically insulating barrier assembly that resides between fingers on a user's hands that are operatively grasping the first and second contours.

* * * * *